United States Patent [19]

Hayashi et al.

[11] 4,141,792
[45] Feb. 27, 1979

[54] COMPOSITION AND METHOD FOR THE QUANTITATIVE DETERMINATION OF PHOSPHOLIPIDS

[76] Inventors: Hiroaki Hayashi, 3-19-16, Shirako, Wako-shi, Saitama-ken; Katsuyuki Watanabe, 1-3-8, Sakura, Setagaya-ku, Tokyo; Toshio Tatano, 2297-67, Ohokahazama, Numazu-shi, Shizuoka-ken, all of Japan

[21] Appl. No.: 825,482

[22] Filed: Aug. 17, 1977

[51] Int. Cl.² ............................................ G01N 31/14
[52] U.S. Cl. ................................. 195/99; 195/103.5 R
[58] Field of Search ........................... 195/103.5 R, 99

[56] References Cited

U.S. PATENT DOCUMENTS 3,759,793  9/1973  Stork et al. ............................ 195/99

OTHER PUBLICATIONS

Bergmeyer, Methods of Enzymatic Analysis, 1974, p. 504.
Dixon et al., Enzymes, 2nd Ed. 1964, pp. 680–683, 732–733 and 738–739.

*Primary Examiner*—Thomas G. Wiseman
*Attorney, Agent, or Firm*—Fitzpatrick, Cella, Harper & Scinto

[57] ABSTRACT

Phospholipid content in a sample is quantitatively determined by enzymatically converting the phospholipids into choline and then determining the amount of the choline.

9 Claims, No Drawings

COMPOSITION AND METHOD FOR THE QUANTITATIVE DETERMINATION OF PHOSPHOLIPIDS

BACKGROUND OF THE INVENTION

The present invention relates generally to an improved composition and method for the quantitative determination of phospholipids in a sample. More specifically, the invention is concerned with a diagnostic agent useful in the quantitative determination of phospholipids in blood serum.

Phospholipids are found in serum, egg, meat, vegetables and the like. It is important to determine the phospholipid content in such substances for diagnosing disease, dietetics, etc. In this regard, medical science has recognized the usefulness of determining the content of phospholipids in blood serum as an aid in diagnosing disease such as hypercholesteremia, liver disease and the like.

A number of tests, techniques and methods have been proposed and are being used to measure or estimate the amount of phospholids in the blood. Among the known methods, more widely used conventional methods are colorimetric procedures utilizing molybdate. Some of these procedures depend upon the conversion of phospholipid to inorganic phosphorous by incinerating a sample; reacting the phosphorous with molybdate to form a phosphomolybdic acid; reducing the phosphomolybdic acid with a reducing agent to form molybdenum blue; and measuring the absorption color of the molybdenum blue. [J. Lab. Clin. Med. Vol. 35, 155 (1950); J. Biol. Chem. Vol. 234, 466 (1959); Shinryo Vol. 16, 677 (1963); Rinsho Byori Vol. 10, 194 (1962), ibid. Vol. 15, 853 (1967)].

More recently, a method has been proposed which contemplates the enzymatic conversion of the phospholipids present in the blood specimen to phosphoric acid and the measurement of the color of the reaction solution obtained by reacting the phosphoric acid with molybdate and then reducing the resultant mixture (Yatron Document RM 137-K, Yatron Co., Ltd.).

The known methods for the quantitative determination of phosphlipids suffer from one or more of the disadvantages of requiring highly skilled laboratory techniques, requiring a great deal of time to perform, not giving consistently precise results and requiring blank measurments owing to interference of the phosphorous contained in the sample and vessels.

SUMMARY OF THE INVENTION

The present invention provides a simple, practical and economical diagnostic colorimetric method for detecting the presence of phospholipids in serum and making a precise quantitative determination thereof. The method offers the advantages of extremely rapid color development and maintenance of color value for a long period of time. Further, this method may be conducted by personnel unskilled in laboratory techniques.

Furthermore, the method of the present invention provides an all all-enzymatic determination of the phospholipids and, therefore, a decided improvement of routine medical diagnosis plus an adaptability of the method for automatic analysis apparatus.

The present invention is based upon the following combination of enzymatic reactions:

Phospholipids such as lecithin, sphingomyelin, lysolecithin, cephalin, phosphatidylserine, etc. are present in blood serum. Among these phospholipids in serum, the total amount of lecithin, sphingomyelin and lysolecithin corresponds to about 95% of the amount of total phospholipids in various samples of serum. These three phospholipids are converted to choline by an enzymatic reaction.

The amount of the reduced form of acceptor produced in the enzymatic conversion of choline to glycine betaine aldehyde in the presence of choline dehydrogenase (hereinafter referred to as CLDH) and hydrogen acceptor is directly proportional to the amount of phospholipid in the blood serum.

Further, the amount of the reduced form of nicotinamide adenine dinucleotide (hereinafter referred to as NADH) produced in the enzymatic conversion of glycine betaine aldehyde to betaine aldehyde in the presence of betaine aldehyde dehydrogenase (hereinafter referred to as BADH) and nicotinamide adenine dinucleotide (hereinafter referred to as NAD) or consumed NAD in the enzymatic reaction is also directly proportional to the amount of phospholipid in the blood serum.

The reduced form of acceptor thus produced can then be detected by measuring the absorption of the color of the reaction solution at a wave length of from 400 to 700 nm.

The NADH thus produced may also be detected by measuring the absorption of the reaction solution at a wave length of 340 nm.

The amount of consumed NAD can be calculated by subtracting the remaining NAD from the added NAD. The remaining NAD in the reaction solution can be detected by measuring the absorption of the reaction solution at a wave length of from 260 to 280 nm.

These reactions are known individually. That is, lecithin catalytically reacts with phosphlipase D (hereinafter referred to as PLD) to form choline [Reaction I, J. Biol. Chem. Vol. 231, 703 (1958), ibid, Vol. 172, 191 (1948)]. Sphingomyelin and lecithin catalytically react with phospholipase C (hereinafter referred to as PLC) to form phosphoryl choline [Reaction II, Biochem. J. Vol. 35, 884 (1946); Biochem. Biophys. Acta. Vol. 59, 103 (1962)], the phosphoryl choline catalytically reacts with phosphatase to form choline [Reaction III, J. Biol. Chem. Vol. 244, 308 (1969)]. Lysolecithin catalytically reacts with phospholipase B (hereinafter referred to as PLB) to form glycerophosphorylcholine [Reaction IV, "Biochemist's Handbook" E. & F. N. Spou Ltd. 282 (1961); Nature Vol. 169, 29 (1952); Biochem. J. Vol. 71, 615 (1959)], the glycerophosphorylcholine catalytically reacts with glycerophosphorylcholine diesterase (hereinafter referred to as GPD) to form choline [Reaction V, J. Biol. Chem. Vol. 206, 647 (1954); Biochem. J. Vol. 62, 689 (1956)].

The choline formed in the reaction described above, catalytically reacts with CLDH in the presence of a hydrogen acceptor to form glycerine betaine aldehyde and reduced form of acceptor [Reaction VI, Agr. Biol. Chem. Vol. 39, 1513 (1975)]. The glycerine betaine aldehyde catalytically reacts with BADH in the presence of NAD to form glycine betaine and NADH [Reaction VII, J. Biol. Chem. Vol. 209, 511 (1954)].

The enzymatic reactions described above are schematically represented as follows:

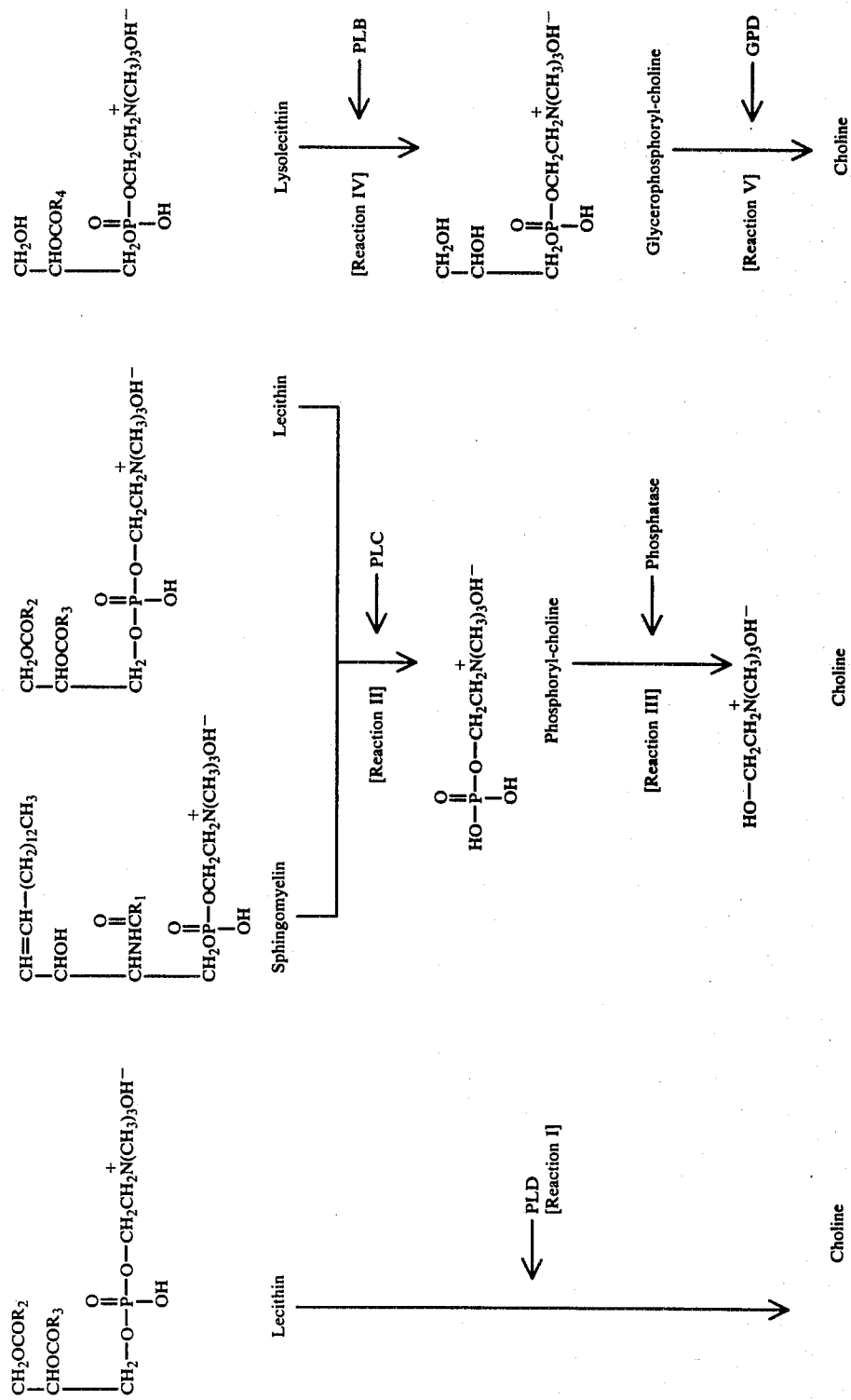

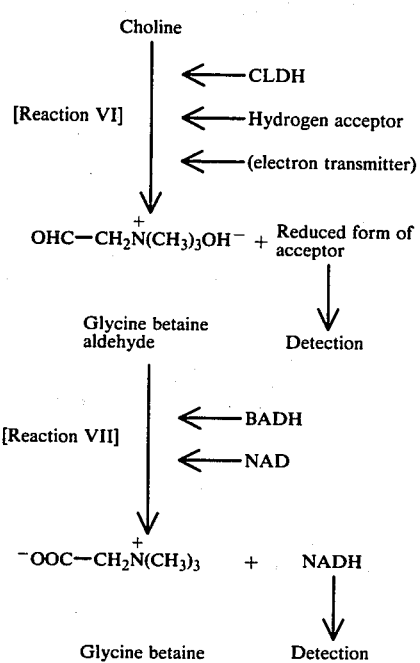

where $R_1$, $R_2$ and $R_3$ represent hydrocarbon groups.

The quantitative determination of lecithin content in a sample is carried out according to the process consisting of Reactions I and VI (hereinafter referred to as Process D) or Reactions I, VI and VII (hereinafter referred to as Process D').

The quantitative determination of total content of sphingomyelin and lecithin in a sample is carried out according to the process consisting of Reactions II, III and VI (hereinafter referred to as Process C) or Reactions II, III, VI and VII (hereinafter referred to as Process C').

The quantitative determination of lysolecithin content in a sample is carried out according to the process consisting of Reactions IV, V and VI (hereinafter referred to as Process B) or Reactions IV, V, VI and VII (hereinafter referred to as Process B').

The quantitative determination of total content of lecithin, sphingomyelin and lysolecithin is carried out according to Processes C and B, Processes C and B', Processes C' and B, or Processes C' and B'.

DETAILED DESCRIPTION OF THE INVENTION

Broadly, the present invention comprises the combination of a system for converting phospholipids in a sample to choline and a system for detecting the so-produced choline.

The system for converting the phospholipids to choline comprises one or more enzymes selected from the group consisting of PLD, PLC and phosphatase, and PLB and GPD.

The choline detecting system comprises CLDH and a hydrogen acceptor or further comprises BADH and NAD and if necessary, comprises an electron transmitter.

Additional subject matter of the invention is a novel reagent composition for converting of phospholipid in a sample to choline which comprises, as a first component, one or more enzymes selected from the group consisting of PLD, PLC and phosphatase, and PLB and GPD; and a second component comprising a choline detecting reagent.

According to the present invention, the quantitative determination of phospholipids may be performed by conducting the individual reactions stepwise. That is, the enzyme reactions are divided into any desired group and after completion of the reaction of the preceding step, the successive enzymes are added thereto, and the reaction of the next step is allowed to proceed. After completion of Reaction VI, the absorption of the visible part of the colored reaction solution by formation of the reduced form of acceptor is measured or after completion of Reaction VII, the absorption of the ultraviolet part of the reaction solution is measured for detecting NADH formed or the remaining NAD. The absorption values obtained by one or more of the above-steps are compared with a calibration curve obtained by carrying out the above-steps on the standard compound, whereby the content of the phospholipids in a sample is determined.

According to the present invention, the presently preferred method for the quantitative determination of phospholipids in a sample is carried out by subjecting a sample to reaction with a reagent consisting of enzymes for converting phospholipids to choline, CLDH and a hydrogen acceptor; and, if necessary, BADH, NAD, an electron transmitter, surfactant, etc. in a buffer solution.

Enzymes used in the present invention are known and those obtained from various sources may be used.

Any PLD may be used so long as it acts only on lecithin among phospholipids. Suitable PLD are obtained from cabbage or the like by extraction and purification and are commercially available from such sources as Sigma Co., U.S.A. and Boehringer Mannheim Co., West Germany.

Any PLC may be used so long as it acts only on sphingomyelin and lecithin among phospholipids. Suitable PLC are obtained from cell bodies of microorganism belonging to *Escherichia coli* by extraction and purification and are commercially available from such sources as Worthington Co., U.S.A. as Catalog No. 5130 and Baehringer Mannheim Co., West Germany, as catalog No. 15429.

Phosphatase obtained from cell bodies of microorganisms belonging to the species *Clostridium perfringens* or *Clostridium welchii* or the like by extraction and purification may be used and are commercially available from such sources as Worthington Co. as Catalog No. 5640 and Sigma Co., U.S.A. as Catalog No. P 7633, etc.

Any PLB may be used so long as it acts only on lysolecithin among phospholipids. Suitable PLB may be obtained from cell bodies of microorganisms belonging to the species *Penicillium notatum* by extraction [Biochem. J. Vol. 70, 559 (1958)]. Those extracted from mucous membranes of livers and intestines of rats, oxen, and pigs, etc. are also appropriate.

Suitable GPD may be obtained from cell bodies of microorganisms belonging to the species *Serratia plymuthicum* by extraction [J. Biol. Chem. Vol. 206, 647 (1954)]. Those extracted from livers of rats, oxen, and pigs [Biochem. J., vol. 62, 689 (1956)], etc. are also appropriate.

Suitable CLDH may be obtained from cell bodies of microorganisms belonging to the species *Pseudomonas aeruginosa*, [Agr. Biol. Chem. Vol. 39, 1513 – 1514 (1975)]. Those extracted from mitochondria of rats [J. Biol. Chem. Vol. 234, 1605 (1959)], etc. are also appropriate.

Suitable BADH may be extracted from cell bodies of microorganisms belonging to the species *Pseudomonas aeruginosa* [Agr. Biol. Chem. Vol. 39, 1513 – 1514 (1975)]. Those purified from a supernatant of homogenate of rat livers [J. Biol. Chem. Vol. 209, 511 (1954)], etc. are also appropriate.

An amount of enzymes to be used to that of phospholipid is determined in such a range that the detecting operation can be exactly carried out. That is, the following amount of enzymes may be used to one $\mu$g of phospholipid;

0.005 – 1 IU for PLD, 0.005 – 1 IU for PLC, 0.005 – 1 IU for PLB, 0.005 – 50 IU for phosphatase, 0.005 – 1 IU for GPD, 0.1 – 50 IU for CLDH, 0.1 – 100 IU for BADH.

The foregoing enzymes are used in an appropriate buffer solution. Preferably concentrations of the enzymes in the buffer solution are 0.01 – 1 IU/ml for PLD; 0.01 – 1 IU/ml for PLC; 0.01 – 1 IU/ml for PLB; 0.1 – 50 IU/ml for phosphatase; 0.01 – 1 IU/ml for GPD; 0.1 – 50 IU/ml for CLDH; and 0.1 – 100 IU/ml for BADH. IU is an international unit of enzyme factor; and the factor capable of decomposing 1 $\mu$ mole of substrate in one minute is defined as 1 IU, i.e. 1 IU = $\mu$ mol/min.

It is desirable to provide the buffer solution at a pH in the range of about from 5.0 to 10.0, preferably from 6.5 to 7.5. For this purpose, buffers which may be used include phosphate, succinate, citrate, borate, acetate, glycylglycinate, tris-malonate as well as other buffers which are generally effective within the pH range of from 5.0 to 10.0.

The concentration of the buffer is not critical. However, it is preferred to use a relatively dilute buffer solution and for this purpose a 0.1 – 0.2 mol/l solution is recommended.

Examples of the hydrogen acceptor are 3,3'-(3,3'-dimethoxy-4,4'-biphenylene)-bis-[2-(p-nitrophenyl)-5-phenyl-2H-tetrazolium chloride] (hereinafter referred to as nitro-TB), (3,3'-dimethoxy-4,4'-biphenylene-bis [2,5-bis (p-nitrophenyl)-2H-tetrazolium chloride] (hereinafter referred to as TNTB), 3-(p-indophenyl-2-(p-nitrophenyl)-5-phenyl-2H-tetrazolium chloride (hereinafter referred to as INT), 2,6-dichlorophenyl-indophenol (hereinafter referred to as DCPIP) and NAD.

When DCPIP is used, it is used with an electron transmitter such as phenazine methosulfate and the like which accepts an electron from choline and donates it to DCPIP.

Since NAD is liable to be converted to NADH by enzymes, the coenzyme of which is NAD, there is sometimes cause for an error when there are such enzymes in the reaction system. It is, therefore, preferable to avoid such combinations.

Preferable concentration of the hydrogen acceptor in the buffer solution is 0.1 – 500 mmol/l.

Preferable concentration of the electron transmitter is 0.1 – 50 mmol/l.

Typical samples in which the amount of phospholipids would be determined, include living components such as serum, liver, etc. and various foods such as vegetable oil, fish oil, vegetables, etc. When the sample is solid it should be ground and then subjected to extraction with water or a small amount of organic solvent such as alcohol, chloroform or the like. On the other hand, when the sample is an oil, a surfactant may be added to the reagent solution to improve the affinity with the reagent solution. Suitable surfactants include such higher alcohols as polyethyleneglycol, etc. Preferably, the concentration of the surfactant in the reagent solution is 0.01 – 5 g/l.

The enzymatic reactions are carried out at 20° to 45° C., preferably 30° to 40° C., at pH 5 to 10, for 4 to 60 minutes.

After completion of the enzymatic reactions, the absorption of the reaction solution is measured by utilizing a spectrophotometer, or the like.

When the amount of the formation of reduced form of acceptor is determined, the absorption of visible part of the reaction solution is measured at a wave length in a range of 400 to 700 nm.

When NAD is used as a hydrogen acceptor in Reaction VI, the quantitative determination of reduced form of acceptor, i.e. NADH formed in Reaction VI is carried out by measuring the absorption of the reaction solution at a wave length of 340 nm.

When the amount of NADH is determined, the absorption of ultraviolet part of the reaction solution is measured at 340 nm and when the amount of remaining NAD is determined, the absorption is measured at 260 – 280 nm.

The colors developed in the reaction by using nitro-TB, TNTB, INT and DCPIP as the hydrogen acceptor are blue, red-brown, red (or violet) and red-blue, respectively.

When NAD is used as a hydrogen acceptor in Reaction VI and the quantitative determination of phospholipid is carried out by measuring the amount of NADH produced after completion of Reaction VII, the quantitative value of NADH determined represents total sum of NADH formed in Reactions VI and VII, and therefore the amount of NADH formed in Reaction VI is taken into consideration. Reaction VII usually proceeds to 100% and thus the amount of NADH formed in Reaction VII can be presumed to be 178 of said sum value.

The composition of the present invention may be used in various forms. For example, the ingredients may be mixed in liquid form or in powder form. The liquid formulation may be readily reconstituted for later use simply by the addition of water or buffer solution. The powders, if desired, may be tableted for convenience in use.

Practice of certain specific embodiments of the invention is illustrated by the following representative examples.

EXAMPLE 1

Quantitative determination of content of lecithin, sphingomyelin and lysolecithin in normal human blood serum.

In this example, 20 $\mu$l of blood serum is added to 3 ml of 0.15 mol/l phosphate buffer solution (pH 7.2) containing 0.04 IU of PLC, 5 IU of phosphatase, 0.014 IU of PLB, 0.014 IU of GPD, 5 IU of CLDH and 0.6 mmol of TNTB.

The enzyamtic reaction is allowed to proceed for 15 min. at 37° C. After completion of the reaction, the absorption of the reaction solution at 550 millimicrons is measured with a spectrophotometer to determine the content of reduced form of acceptor formed in the solution.

The content of the phospholipids is obtained by comparing the absorption value with a standard curve obtained by applying the method described above on a standard sample of lecithin (produced by Sigma Co., Letc., Catalogue No. L-2004).

As a control, the same serum is subjected to extraction using a chloroform-methanol solution according to the Folch extraction method. The resulting extract is oxidized by using perchloric acid to form an inorganic phosphorous and a molybdate; and, thereafter, hydrazine sulfate is added to the resulting solution to form a colored solution. Absorption of the color developed at a wave length of 700 nm is measured with a spectrophotometer [Rinsho Byori, Vol. 10, 194 (1962)].

The samples are measured 10 times for each method described above. The results are given in Table 1.

Table 1

| Test run No. | Content of Phospholipids (mg/dl) | |
|---|---|---|
| | Present method | Prior method |
| 1 | 185.3 | 189.3 |
| 2 | 187.2 | 195.2 |
| 3 | 184.4 | 199.4 |
| 4 | 186.7 | 190.8 |
| 5 | 185.1 | 187.2 |
| 6 | 181.9 | 193.6 |
| 7 | 188.2 | 195.1 |
| 8 | 187.5 | 188.8 |
| 9 | 186.3 | 192.3 |
| 10 | 184.6 | 190.5 |
| Average | 185.7 | 192.2 |
| Standard deviation | 1.85 | 3.68 |
| Coefficient of variation | 0.99% | 1.91% |

As is apparent from Table 1, the standard deviation and coefficient of variation in the present method are less than those of the known method.

To make a comparison with the prior known method as to the content of total phospholipids, multiplication by a factor of 1.0416 gives an average of the content of total phosphlipids, 193.4 mg/dl, almost the same numerical value as that of the prior method.

EXAMPLE 2

Quantitative determination of lecithin, sphingomyelin and lysolecithin in patient serum (II b type).

In this example, 20 μl of patient serum is added to 3 ml of 0.15 mol/l tris-buffer solution (pH 7.2) containing 0.04 IU of PLC, 5 IU of phosphatase, 0.014 IU of PLB, 0.014 IU of GPD, 5 IU of CLDH, 5 IU of BADH and 0.09 mmol of NAD.

The enzymatic reaction is allowed to proceed for 15 min. at 37° C. After completion of the reaction, the absorption of the reaction solution at 340 nm millimicrons is measured at various time intervals using a spectrophotometer to determine the content of NADH formed in the solution. The values are given in Table 2.

Table 2

| | Content of total phospholipid (mg/dl) |
|---|---|
| 30 seconds | 305.2 |
| 1 minute | 312.1 |
| 5 minutes | 314.3 |
| 15 minutes | 313.0 |

As is apparent from the values set forth in Table 2, the quantative determination of total phospholipid according to the present method can be carried out in a short period of time.

EXAMPLE 3

Quantitative determination of content of total phospholipid in serum.

In this example, the procedures described in Example 1 are repeated except 0.6 mmol of INT is used instead of TNTB, and normal human serum and patient serums (IIa, IIb and IV types) are used.

The results are given in Table 3.

The content of total phospholipid, according to the present method, is obtained by multiplication by a value of 1.0416.

Table 3

| Serum | The content of total phospholipid (mg/dl) | |
|---|---|---|
| | Present method | Prior method |
| Normal human | 194.2 ± 14.0 | 201.5 ± 32.3 |
| II a type | 275.3 ± 15.4 | 278.7 ± 40.2 |
| II b type | 341.0 ± 19.5 | 348.2 ± 51.2 |
| IV type | 273.5 ± 12.3 | 263.2 ± 52.3 |

EXAMPLE 4

Quantitative determination of lysolecithin content in patient blood serum.

In this example, 100 μl of blood serum is added to 3 ml of 0.15 mol/l phosphate buffer solution (pH 7.2) containing 0.014 IU of PLB, 0.014 IU of GPD, 5 IU of CLDH and 0.6 mmol of TNTB.

The enzymatic reaction is allowed to proceed for 15 minutes at 37° C. After completion of the reaction, the absorption of the reaction solution is measured with a spectro-photometer at a wave length of 550 nm. The red-brown color of the reaction solution is compared with a calibration curve obtained by using a standard compound.

As a control (known method), the same serum is developed by thin layer chromatography using silica gel. The resultant sample is incinerated and a color is developed by using a molybdic acid reagent. The color is measured with a densitometer. The results are given in Table 4.

Table 4

| Test run No. | Content of lysolecithin (mg/dl) | |
|---|---|---|
| | Present method | Prior Method |
| 1 | 35.36 | 35.45 |
| 2 | 35.82 | 36.85 |
| 3 | 35.14 | 34.67 |
| 4 | 35.38 | 35.59 |
| 5 | 34.98 | 36.98 |
| 6 | 35.67 | 35.56 |
| 7 | 35.28 | 36.02 |
| 8 | 35.43 | 35.95 |
| 9 | 35.33 | 34.38 |
| 10 | 35.87 | 35.21 |
| Average | 35.42 | 35.66 |
| Standard deviation | 0.28 | 0.83 |
| Coefficient of variation | 0.79% | 2.32% |

EXAMPLE 5

In this example, 100 μl of normal human blood serum is added to 3 ml of 0.15 mol/l glycylglycine buffer solution (pH 7.2) containing 0.04 IU of PLB, 0.04 IU of GPD, 5 IU of CLDH, 5 IU of BADH and 0.09 mmol of NAD. The enzymatic reaction is allowed to proceed for 15 minutes at 37° C.

After completion of the reaction, the absorption of the reaction solution at 340 nm is measured with a spectrophotometer to determine the content of NADH formed in the solution.

The content of lysolecithin is obtained by comparing the absorption value with a standard curve obtained by applying the above method on a known quantity of lysolecithin (made by Sigma Co., Ltd., Catalogue No. L 6626). The results are given in Table 5.

Table 5

| Sample No. | Content of lysolecithin (mg/dl) | | | |
|---|---|---|---|---|
| | 30 sec. | 1 min. | 5 min. | 15 min. |
| 1 | 13.25 | 17.66 | 17.69 | 17.58 |
| 2 | 11.65 | 15.35 | 15.36 | 15.32 |
| 3 | 15.23 | 20.10 | 20.11 | 20.08 |
| 4 | 12.51 | 16.83 | 16.86 | 16.75 |
| 5 | 11.23 | 14.92 | 14.95 | 14.89 |

EXAMPLE 6

Quantitative determination of lysolecithin content in various serums.

In this example, the procedure described in Example 4 is repeated except 0.6 mmol of INT is used instead of TNTB and 10 samples each of normal human blood serum and patient serums (IIa, IIb and IV types) are used.

The results are given in Table 6.

Table 6

| Kind of serum | Content of lysolecithin (mg/dl) | |
|---|---|---|
| | Present method | Prior method |
| Normal human serum | 17.63 ± 4.66 | 18.43 ± 5.42 |
| Patient serum IIa type | 25.25 ± 5.70 | 26.26 ± 7.41 |
| Patient serum IIb type | 35.36 ± 9.23 | 35.97 ± 11.45 |
| Patient serum IV type | 27.08 ± 8.64 | 26.84 ± 11.77 |

EXAMPLE 7

Quantitative determination of lecithin content in patient blood serum.

In this example, 20 μl of blood serum is added to 3 ml of 0.15 mol/l phosphate buffer (pH 7.2) containing 0.014 IU of PLD, 5 IU of CLDH and 0.6 mmol of TNTB. The enzymatic reaction is allowed to proceed for 15 minutes at 37° C. After completion of the reaction, the absorption of the reaction solution at 550 nm is measured with a spectrophotometer. The color of the reaction solution is compared with a calibrated color chart obtained according to the method described above using lecithin as a standard compound.

As a control, the procedure of the prior method described in Example 4 is repeated on the same serum. The results are given below in Table 7.

Table 7

| Test run No. | Content of Lecithin (mg/dl) | |
|---|---|---|
| | Present method | Prior method |
| 1 | 126.88 | 126.88 |
| 2 | 128.47 | 130.50 |
| 3 | 126.48 | 138.45 |
| 4 | 124.08 | 117.50 |
| 5 | 123.88 | 118.50 |
| 6 | 128.67 | 113.51 |
| 7 | 127.87 | 141.24 |
| 8 | 126.08 | 114.71 |
| 9 | 124.28 | 124.48 |
| 10 | 129.07 | 134.46 |
| Average | 126.57 | 126.02 |
| Standard deviation | 1.97 | 9.96 |
| Coefficient of variation | 1.55 | 7.90 |

EXAMPLE 8

Quantitative determination of lecithin content in normal human blood serum.

In this example, 20 μl of blood serum is added to 3 ml of 0.15 mol/l glycylglycine buffer solution (pH 7.2) containing 0.04 IU of PLD, 5 IU of CLDH and 0.09 mmol of NAD and the enzymatic reaction is allowed to proceed for 15 minutes at 37° C.

The content of NADH formed in the reaction solution is determined by using a spectrophotometer. An increase in absorbance at 340 nm is monitored for 15 minutes.

The results are given in Table 8.

Table 8

| Sample No. | Content of lecithin (mg/dl) | | | |
|---|---|---|---|---|
| | 3 sec. | 1 min. | 5 min. | 15 min. |
| 1 | 124.6 | 124.8 | 128.3 | 126.61 |
| 2 | 126.8 | 127.7 | 130.1 | 128.1 |
| 3 | 125.2 | 126.0 | 128.6 | 127.2 |
| 4 | 123.8 | 123.7 | 124.4 | 123.8 |
| 5 | 128.6 | 128.4 | 132.0 | 130.7 |

EXAMPLE 9

In this example, the procedure described in Example 7 is repeated except 0.6 mmol of INT is used instead of TNTB and 10 samples each of normal human blood serum and patient blood serums (IIa, IIb and IV types) are used.

The results (average data) are given in Table 9.

Table 9

| Kind of serum | Content of lecithin (mg/ml) | |
|---|---|---|
| | Present method | Prior method |
| Normal human | 128.3 ± 4.8 | 128.85 ± 8.75 |
| IIa type | 175.18 ± 9.8 | 173.68 ± 12.34 |
| IIb type | 219.90 ± 10.8 | 226.05 ± 12.84 |
| IV type | 174.88 ± 11.04 | 173.69 ± 16.72 |

EXAMPLE 10

Quantitative determination of sphingomyelin content in blood serum.

(1) Determination of total content of lecithin and sphingomyelin in blood serum

In this example, 20 μl of blood serum is added to 3 ml (pH 7.2) of 0.15 mol/l phosphate buffer solution containing 0.04 IU of PLC, 5 IU of phosphatase, 5 IU of CLDH and 0.6 mmol of TNTB. The enzymatic reaction is allowed to proceed for 15 min. at 37° C. After completion of the reaction, the absorption of the reaction solution at 550 nm is measured and the absorption value is compared with a calibrated color chart obtained by the determination according to the method described above using a known quantity of L-α-lecithin as a standard compound.

As a result, the total content of lecithin and sphingomyelin is obtained.

(2) Determination of lecithin content in serum

In this example, the procedure described in the above determination of total content of lecithin and sphingomyelin is repeated except using 0.04 IU of PLD in place of PLC and phosphatase.

As a result, the content of lecithin in blood serum is obtained.

The content of sphingomyelin is calculated by subtracting the content of lecithin from the total value.

As a control, the procedure of the known method described in Example 4 is repeated on the same serum. The results are given in Table 10.

Table 10

| Test run No. | Present method (mg/dl) Lecithin + Sphingomyelin | Lecithin | Sphingomyelin | Prior method (mg/dl) |
|---|---|---|---|---|
| 1 | 167.20 | 126.88 | 40.32 | 41.69 |
| 2 | 171.35 | 128.47 | 42.88 | 46.21 |
| 3 | 165.56 | 126.46 | 39.08 | 37.85 |
| 4 | 163.85 | 124.08 | 39.77 | 42.32 |
| 5 | 169.53 | 125.88 | 43.65 | 37.01 |
| 6 | 170.20 | 128.67 | 41.53 | 38.35 |
| 7 | 168.35 | 127.87 | 40.48 | 43.32 |
| 8 | 171.12 | 128.08 | 43.04 | 41.51 |
| 9 | 165.35 | 124.28 | 41.07 | 40.21 |
| 10 | 168.82 | 129.07 | 39.75 | 39.35 |
| Average | 168.13 | 126.97 | 41.15 | 40.78 |
| Standard deviation | 2.57 | 1.78 | 1.57 | 2.80 |
| Coefficient of variation | 1.53 | 1.40 | 3.81 | 6.86 |

EXAMPLE 11

Quantitative determination of sphingomyelin content in blood serum.

(1) Determination of the total content of lecithin and sphingomyelin

In this example, 20 μl of blood serum is added to 3 ml (pH 7.2) of 0.15 mol/l of glycyl-glycine buffer solution containing 0.04 IU of PLC, 5 IU of phosphatase, 5 IU of CLDH, 5 IU of BADH and 0.09 mmol of NAD.

The enzymatic reaction is allowed to proceed for 15 minutes at 37° C. After completion of the reaction, the absorption of the reaction solution at 340 nm is measured to determine NADH formed in the reaction solution with a spectrophotometer. The calibration curve described in Example 10 is used as a calibration curve.

(2) Determination of lecithin content

In this example, the procedure described in the above determination of total content of lecithin and sphingomyelin is repeated except using 0.04 IU of PLD in place of PLC and phosphatase.

The content of sphingomyelin is calculated in the same manner as in Example 10.

The results are given in Table 11.

Table 11

| Test run No. | Present method (mg/dl) Lecithin + Sphingomyelin | Lecithin | Sphingomyelin | Prior method (mg/ml) |
|---|---|---|---|---|
| 1 | 213.6 | 161.3 | 52.3 | 56.3 |
| 2 | 215.4 | 159.6 | 55.8 | 51.7 |
| 3 | 209.5 | 162.1 | 47.4 | 49.6 |
| 4 | 210.3 | 161.2 | 49.1 | 55.8 |
| 5 | 213.2 | 160.8 | 52.4 | 52.7 |
| 6 | 211.2 | 163.0 | 48.2 | 48.6 |
| 7 | 208.9 | 159.4 | 49.5 | 43.8 |
| 8 | 214.3 | 156.3 | 58.0 | 52.8 |
| 9 | 215.0 | 162.1 | 53.9 | 49.6 |
| 10 | 214.2 | 159.6 | 54.8 | 58.4 |
| Average | 212.5 | 160.5 | 52.1 | 51.9 |
| Standard deviation | 2.37 | 1.91 | 3.53 | 4.28 |
| Coefficient of variation | 1.1 | 1.2 | 6.7 | 8.2 |

EXAMPLE 12

In this example, the procedures described in Examples 10 and 11 are repeated on 10 samples of serum. When the quantitative determination of sphingomyelin is calculated, the correlation by combination of the determination of reduced form of acceptor (absorption of visible part) and that of NADH (absorption of ultraviolet part) is studied.

The results are given in Tables 12 and 13.

Table 12

| Sample No. | Method according to Example 10 | | Method according to Example 11 | |
|---|---|---|---|---|
| | P Lecithine + sphingomyelin | Q Lecithin | P' Lecithine + sphingomyelin | Q' Lecithin |
| 1 | 167.2 | 128.4 | 166.7 | 127.9 |
| 2 | 213.3 | 164.1 | 214.5 | 165.3 |
| 3 | 269.8 | 204.2 | 267.3 | 208.3 |
| 4 | 233.6 | 175.2 | 233.8 | 174.5 |
| 5 | 214.5 | 162.4 | 212.3 | 159.9 |
| 6 | 267.9 | 202.3 | 268.3 | 203.1 |
| 7 | 283.2 | 219.9 | 281.9 | 220.1 |
| 8 | 201.0 | 159.3 | 200.3 | 261.1 |
| 9 | 226.7 | 174.9 | 224.3 | 173.8 |
| 10 | 172.4 | 132.1 | 173.1 | 133.0 |

Table 13

| | Content of sphingomyelin (mg/ml) | | | |
|---|---|---|---|---|
| | P − Q | P' − Q' | P − Q' | P' − Q |
| 1 | 38.8 | 38.8 | 39.1 | 38.8 |
| 2 | 49.2 | 49.2 | 48.0 | 50.4 |
| 3 | 65.6 | 59.0 | 61.5 | 63.1 |
| 4 | 58.4 | 59.3 | 59.1 | 58.6 |
| 5 | 52.1 | 52.4 | 54.6 | 49.9 |
| 6 | 65.5 | 65.2 | 64.8 | 66.0 |
| 7 | 63.3 | 61.8 | 63.1 | 62.0 |
| 8 | 41.7 | 39.2 | 39.9 | 41.0 |
| 9 | 51.8 | 50.5 | 52.9 | 49.4 |
| 10 | 40.3 | 40.1 | 39.4 | 41.0 |

Correlation between P and P'
Coefficient of correlation $\gamma = 1.00$, $Y = 0.99X + 1.54$
Correlation between Q and Q'
Coefficient of correlation $\gamma = 1.00$, $Y = 1.02X - 3.03$
Correlation between P-Q and P'-Q'
Coefficient of correlation $\gamma = 0.98$, $Y = 0.93X + 2.56$
Correlation between P-Q' and P'-Q
Coefficient of correlation $\gamma = 0.97$, $Y = 0.96X + 1.82$

What is claimed is:

1. A test composition for the determination of phospholipids in a sample comprising
   a first component comprising at least one enzyme group selected from the groups consisting of (A) phospholipase C and phosphatase and (B) phospholipase B and glycerophosphorylcholine diesterase; and
   a second component comprising a choline dehydrogenase and a hydrogen acceptor selected from the group consisting of 3,3'-(3,3'-dimethoxy-4,4'-biphenylene)-bis-[2-(p-nitrophenyl)-5-phenyl-2H-tetrazolium chloride],3,3'-(3,3'-dimethoxy-4,4'-biphenylene-bis[2,5-bis(p-nitrophenyl)-2H-tetrazolium chloride], 3-(p-indophenyl-2-(p-nitrophenyl)-5-phenyl-2H-tetrazolium chloride, 2,6-dichlorophenyl-indophenol and nicotinamide adenine dinucleotude.

2. The composition of claim 1 further comprising betaine aldehyde dehydrogenase and nicotinamide adenine dinucleotide.

3. The composition of claim 1 wherein said phospholipid is lysolecithin, and said first component is phospholipase B and glycerophosphorylcholine diesterase.

4. The composition of claim 1 wherein said phospholipid comprises lecithin and sphingomyelin, and said first component is phospholipase C and phosphatase.

5. The composition of claim 1 wherein said phospholipid comprises lecithin, sphingomyelin and lysolecithin, and said first component comprises phospholipase B, phospholipase C, phosphatase, and glycerophosphorylcholine diesterase.

6. A test composition for the determination of lecithin in a sample which composition comprises phospholipase D, choline dehydrogenase and a hydrogen acceptor selected from the group consisting of 3,3'-(3,3'-dimethoxy-4,4'-biphenylene)-bis-[2-(p-nitrophenyl)-5-phenyl-2H-tetrazolium chloride], 3,3'-(3,3'-dimethoxy-4,4'-biphenylene-bis[2,5-bis(p-nitrophenyl)-2H-tetrazolium chloride], 3-(p-indophenyl-2-(p-nitrophenyl)-5-phenyl-2H-tetrazolium chloride, 2,6-dichlorophenyl-indophenol and nicotinamide adenine dinucleotide.

7. The composition of claim 6 further comprising betaine aldehyde dehydrogenase and nicotinamide adenine dinucleotide.

8. A methode for determining phospholipid content in a sample by hydrolysis according to an enzymatic reaction which comprises adding said sample to a buffer solution containing choline dehydrogenase, a hydrogen acceptor selected from the group consisting of 3,3'-(3,3'-dimethoxy-4,4'-biphenylene)-bis-[2-(p-nitrophenyl)-5-phenyl-2H-tetrazolium chloride], 3,3'-(3,3'-dimethoxy-4,4'-biphenylene-bis [2,5-bis(p-nitrophenyl)-2H-tetrazolium chloride], 3-(p-indophenyl-2-(p-nitrophenyl)-5-phenyl-2H-tetrazolium chloride, 2,6-dichlorophenyl-indophenol and nicotinamide adenine dinucleotide, and at least one enzyme group selected from the groups consisting of
(A) phospholipase D
(B) phospholipase C and phosphatase, and
(C) phospholipase B and glycerophosphorylcholine diesterase,
thereby effecting an enzymatic conversion of phospholipids to choline in one step with simultaneous reduction of said hydrogen acceptor to reduced form of acceptor; and thereafter determining colorimetrically at a wave length in the range of 400 to 700 nm the color developed.

9. A method for determining phospholipid content in a sample by hydrolysis according to an enyzmatic reaction which comprises adding said sample to a buffer solution containing choline dehydrogenase, a hydrogen acceptor selected from the group consisting of 3,3'-(3,3'-dimethoxy-4,4'-biphenylene)-bis-[2-(p-nitrophenyl)-5-phenyl-2H-tetrazolium chloride], 3,3'-(3,3'-dimethoxy-4,4'-biphenylene-bis [2,5-bis(p-nitrophenyl)-2H-tetrazolium chloride], 3-(p-indophenyl-2-(p-nitrophenyl)-5-phenyl-2H-tetrazolium chloride, 2,6-dichlorophenyl-indophenol and nicotinamide adenine dinucleotide, betaine aldehyde dehydrogenase, nicotinamide adenine dinucleotide (NAD) and at least one enzyme group selected from the groups consisting of
(A) phospholipase D
(B) phospholipase C and phosphatase, and
(C) phospholipase B and glycerophosphorylcholine diesterase,
thereby effecting an enzymatic conversion of phospholipids to choline in one step with simultaneous reduction of NAD to reduced form of NAD (NADH) and determining colorimetrically at a wave length of 340 nm the absorption of the reaction solution.

* * * * *

UNITED STATES PATENT OFFICE
CERTIFICATE OF CORRECTION

Patent No. 4,141,792              Dated February 27, 1979

Inventor(s) HIROAKI HAYASHI, et al.

It is certified that error appears in the above-identified patent and that said Letters Patent are hereby corrected as shown below:

Column 1, line 64, delete "all" (first occurrence);

Column 8, line 38, "178" should be --1/2--;

Column 9, line 2, "Letc." should be --Ltd.--;

Column 14, claim 5, should read as follows:

--5. A test composition for the determination of total content of phospholipids in a sample represented by lecithin, sphingomyelin and lysolecithin which comprises, a first component comprising phospholipase B, phospholipase C, phosphotase and glycerophosphorylcholine diesterase; and

UNITED STATES PATENT OFFICE
CERTIFICATE OF CORRECTION

Patent No. 4,141,792  Dated February 27, 1979

Inventor(s) HIROAKI HAYASHI, et al.

It is certified that error appears in the above-identified patent and that said Letters Patent are hereby corrected as shown below:

a second component comprising choline dehydrogenase and a hydrogen acceptor selected from the group consisting of 3,3'-(3,3'-dimethoxy-4,4'-biphenylene)-bis-[2-p-nitrophenyl)-5-phenyl-2H-tetrazolium chloride], 3,3'-(3,3'-dimethoxy-4,4'-biphenylene-bis-[2,5-bis-(p-nitrophenyl)-2H-tetrazolium chloride], 3-(p-indophenyl)-2-(p-nitrophenyl)-5-phenyl-2H-tetrazolium chloride, 2,6-dichlorophenylindophenol and nicotinamide adenine dinucleotide.--

Column 15, line 17, "methode" should be --method--.

Signed and Sealed this

Sixteenth Day of October 1979

[SEAL]

Attest:

RUTH C. MASON
Attesting Officer

LUTRELLE F. PARKER
Acting Commissioner of Patents and Trademarks

UNITED STATES PATENT AND TRADEMARK OFFICE
CERTIFICATE OF CORRECTION

PATENT NO. : 4,141,792

DATED : February 27, 1979

INVENTOR(S) : HIROAKI HAYASHI, et al.

It is certified that error appears in the above-identified patent and that said Letters Patent are hereby corrected as shown below:

Page 1, add --[30] Foreign Application Priority Data

August 19, 1976 Japan....... 51-98233 --.

Signed and Sealed this

Tenth Day of June 1980

[SEAL]

Attest:

SIDNEY A. DIAMOND

Attesting Officer

Commissioner of Patents and Trademarks